United States Patent
Jean et al.

(10) Patent No.: US 6,987,393 B2
(45) Date of Patent: Jan. 17, 2006

(54) ULTRA-WIDE BAND PULSE DISPERSION SPECTROMETRY METHOD AND APPARATUS PROVIDING MULTI-COMPONENT COMPOSITION ANALYSIS

(75) Inventors: Buford Randall Jean, Austin, TX (US); Frederick Lynn Whitehead, Austin, TX (US)

(73) Assignee: Rhino Analytics, L.P., Cedar Park, TX (US)

(*) Notice: Subject to any disclaimer, the term of this patent is extended or adjusted under 35 U.S.C. 154(b) by 0 days.

(21) Appl. No.: 10/487,127

(22) PCT Filed: Aug. 22, 2002

(86) PCT No.: PCT/US02/26641

§ 371 (c)(1),
(2), (4) Date: Feb. 19, 2004

(87) PCT Pub. No.: WO03/019207

PCT Pub. Date: Mar. 6, 2003

(65) Prior Publication Data

US 2004/0239337 A1    Dec. 2, 2004

Related U.S. Application Data

(60) Provisional application No. 60/314,782, filed on Aug. 24, 2001.

(51) Int. Cl.
G01R 27/06    (2006.01)
G01N 27/00    (2006.01)

(52) U.S. Cl. .................................. 324/644; 324/710
(58) Field of Classification Search ............ 324/638, 324/637, 639, 642, 710
See application file for complete search history.

(56) References Cited

U.S. PATENT DOCUMENTS

| | | | | |
|---|---|---|---|---|
| 3,107,329 A | * | 10/1963 | McSkimin | 324/647 |
| 4,135,131 A | * | 1/1979 | Larsen et al. | 324/639 |
| 4,639,669 A | * | 1/1987 | Howard et al. | 324/239 |
| 5,132,623 A | * | 7/1992 | De et al. | 324/338 |
| 5,177,445 A | * | 1/1993 | Cross | 324/637 |
| 5,227,621 A | * | 7/1993 | Kim et al. | 250/214.1 |
| 6,178,817 B1 | * | 1/2001 | Hewelt et al. | 73/290 V |
| 6,335,625 B1 | * | 1/2002 | Bryant et al. | 324/637 |
| 6,906,662 B2 | * | 6/2005 | Faust et al. | 342/124 |

* cited by examiner

*Primary Examiner*—Anjan Deb
(74) *Attorney, Agent, or Firm*—Patrick Stellitano

(57) ABSTRACT

Apparatus and methods of obtaining information concerning a substance (57) is provided by applying pulses (91, 92, 93) of electromagnetic energy to the substance (57) and evaluating the response of the substance to the electromagnetic energy. The pulses (91, 92, 93) generated by a source (51) are of sufficiently short duration to generate a very broad frequency band of energy. The pulsed energy is directed to the substance (57) to be processed and energy pulses (91, 92, 93) passing through the substance (57) are received (56) and analyzed (66) to determine the properties of substance (57).

23 Claims, 8 Drawing Sheets

ULTRA-WIDE BAND PULSE DISPERSION SPECTROMETRY METHOD AND APPARATUS PROVIDING MULTI-COMPONENT COMPOSITION ANALYSIS

CROSS REFERENCE TO RELATED APPLICATION

Cross-reference is made to Rule 371 application, PCT/US02/26641, filed Aug. 22, 2002, which claims the benefit of Provisional Application No. 60/314,782, filed Aug. 24, 2001.

TECHNICAL FIELD OF THE INVENTION

The present invention relates to the field of analysis of the composition of substances using electromagnetic energy instrumentation.

BACKGROUND OF THE INVENTION

Microwave composition analysis instruments are finding increasing utility throughout industry to solve a wide range of measurement problems. Such instruments have been demonstrated to improve process efficiency, enhance product quality, and to allow automatic control of process parameters in food, chemical, petroleum, pulp and paper, and a host of other material processing and monitoring applications.

Industrial sensors and composition analyzers are used to obtain information concerning the composition of a substance to be processed by analyzing the response of the substance to electromagnetic energy. This response depends upon the constitutive electromagnetic parameters of the individual component materials comprising the substance. These parameters comprise permittivity, permeability, and conductivity. The sensors usually do not compute the actual values of the electrical parameters of each component material comprising the substance, but instead, the sensors are calibrated to yield a composition reading based upon measured signal properties that directly depend upon the electrical characteristics of the composite substance.

It is well known that the constitutive electrical properties of materials, that is, the complex electrical permittivity and the magnetic permeability, are frequency dependent. Thus, information concerning the composition of the substance can be obtained by exposing the substance to be analyzed to different frequencies and analyzing the response at each frequency. Typically, the method for measuring the frequency-dependent characteristics of materials involves sequentially generating each frequency of interest, exposing the substance to energy generated at each frequency, measuring at each frequency a response of the substance to the energy to which it is exposed, and then analyzing some aspect of the response of the material to determine the desired parameter value at each of those frequencies.

For example, a well-known technique for determining the complex permittivity of a material is to use an open-ended coaxial transmission line brought into direct contact with the material under test. A signal is applied to the transmission line and a reflection measurement is made at a number of frequencies. A permittivity value is then computed for each frequency, based upon the known characteristics of the transmission line and the reflection properties as a function of the material's permittivity as governed by Maxwell's equations.

In U.S. Pat. No. 5,331,284, Jean, et. al., describe a meter and method that is presently being marketed as a guided microwave spectrometer (GMS) system that uses a different approach for obtaining frequency dependent information. In the GMS system, a broad-band measurement is performed by stepping sequentially through a range of frequencies and measuring the transmission cutoff characteristics of a waveguide that contains the material under test. By analyzing this spectral response of the waveguide, the effects of the frequency-dependent electrical properties can be calibrated to yield multi-component analysis of various mixtures.

A host of microwave composition analyzers are on the market at present. Among those available are instruments that measure amplitude, phase, time of flight, cutoff frequency characteristics, oscillator load pull, multiple path interference, or tuned circuit resonance, either singularly or in various combinations. There are sensors that make use of reflection or transmission or both. Some instruments employ multiple frequencies or other multi-dimensional measurements of signal properties to provide multi-component analysis for certain types of mixtures.

For further background of microwave composition measurement technologies and for an extensive, though not exhaustive, list of applications for such technology refer to Jean et al., U.S. Pat. No. 5,331,284. The present invention may be advantageously employed in such applications therein listed, and included here by reference. For each of the technologies represented by the above list and those identified by reference, certain common problems exist: the microwave components comprising the instrumentation are expensive, the instrumentation lacks flexibility, or does not provide adequate performance.

In a related field of measurement, that of microwave radar tank level gauging, a breakthrough technology has emerged. Microwave level gauging radars are now available that employ Ultra-Wide-Band (UWB) pulse technology. UWB pulses are inexpensive to generate and receivers are available that allow precise distance measurement at low cost while consuming very small levels of electrical power. Application of UWB pulse technology has not been limited to radar distance measurement. UWB technology has also been identified as useful for dielectric constant measurement through time-of-flight measurement. See, for example, "Microradar Sensors for the New Millennium" available from the website of McEwan Technologies, LLC, which may be found at the following URL address: http://www.ge-tradar.com/patents.shtml.

A somewhat unrelated yet important field of use for ultra-wideband pulses recently to emerge is that of wireless communications. Although the communications field of use is not directly related to the measurement applications addressed here, these measurement applications can directly benefit from the technology being developed for communications purposes. Wireless applications have grown to the point that at least one company has been formed for the express purpose of exploiting this technology and is developing integrated circuit chipsets to generate and process UWB pulses ("Pulse ON© Time Modulated Ultra-Wideband For Wireless Applications", Time Domain, 7057 Old Madison Pike, Huntsville, Ak. 35806).

The advantage of UWB communication methods is that a limited frequency spectrum resource can be made available to multiple users without interference. The methods used to avoid interference among multiple communication channels can be applied to process control measurement devices as well, even though the uses of the spectral content of the signals may be quite different from that of communication between personal telephones or computers.

Process engineers and users of composition analysis instruments are no longer doubtful of the benefits that attain by applying microwave technology to difficult measurement situations. Today the primary impediment to the widespread application of microwave sensing instruments remains their high cost, lack of flexibility, and performance limitations. Accordingly, there is a need for an invention that overcomes these and other limitations of the prior art.

SUMMARY OF THE INVENTION

In view of the recognized need for a low cost solution for a wide range of industrial composition measurement applications, particularly in the microwave frequency domain, and in view of the advancement in high frequency circuit technology, the present invention teaches a new and important method for composition analysis using the unique characteristics of ultra-wideband pulses and the propagation of such pulses in a dispersive channel or medium.

The present invention overcomes prior art limitations by providing systems and methods employing Ultra-Wide-Band (UWB) pulse technology. The UWB pulse dispersion spectrometry methods and apparatus provided by the present invention remove the high cost barrier of electromagnetic composition analysis, yield improved performance, and offer greater flexibility and ease of operation and implementation.

According to one aspect of the invention, Ultra-Wide-Band (UWB) pulse technology is employed to provide a sequence of electromagnetic energy pulses of relatively short duration. These pulses are communicated to the substance to be analyzed. The response of the substance to the pulses is measured and analyzed to determine properties of the substance. Knowledge of the properties of the substance may then be usefully employed in an industrial or other process involving the substance.

According to the present invention, a source for generating Ultra-Wide Band (UWB) pulses of electromagnetic energy is provided. The pulses generated by the source are of sufficiently short duration to generate a very broad frequency band of energy. This pulsed energy is directed toward a substance to be processed. Energy pulses passing through the substance or scattered from the substance are received and analyzed to determine properties of the substance.

According to another aspect of the invention, an equivalent time sampling pulse receiver may be employed to receive the pulsed energy that has interacted with the substance. The substance interacting with the pulsed energy provided by the source will produce dispersion of the pulses. This dispersion is a function of the characteristics of the substance and affects the shape, duration, phase, and time of arrival of the energy pulses coupled to the sampling pulse receiver. The pulse receiver samples each received pulse to produce an acquired sample representation that is analyzed by processing electronics to determine material parameters of interest.

According to another aspect of the invention, the dispersed energy pulses sampled by the receiver can be analyzed by comparison to the amplitude and timing of the input pulses, which are communicated from the source of the pulses to the receiver through a reference line to determine material parameters of interest.

According to the methods of the present invention, the Ultra-Wide-Band (UWB) energy pulses may be communicated to the substance by coupling them into and out of a measurement cell containing the substance. Such a measurement cell can be specially constructed or may, for example, simply be a section of pipe through which the substance flows in an industrial process.

According to another aspect of the invention, the UWB pulses are communicated to the substance by an antenna. Energy transmitted through the substance is received by an antenna and communicated to a receiver. Also, energy scattered by the substance may be received by an antenna and communicated to the receiver. The received signals may be analyzed and the time of arrival of the signals can be compared to determine information concerning the substance.

According to another aspect of the invention, a pulse generator transmits a pulsed signal that is caused to interact with a substance to be processed to produce a response signal. A receiver processes the response signal by comparing a time of arrival of a pulse in the response signal arising from energy scattered from the substance to a time of arrival of a different pulse in the response signal arising from energy transmitted through the substance.

According to another aspect of the invention, a response signal arising from interaction of the substance with a pulse of energy is transformed to produce a signal indicative of a response of the substance to energy at different, frequencies within the range of frequencies in the spectrum of the pulsed signal. More generally, the response signal may be processed by performing a transformation of the response signal to produce a resultant signal that is a function of a variable of the transformation.

According to another aspect of the invention, a signal arising from interaction of the substance with a sequence of energy pulses comprises a plurality of pulses that are sampled to produce an acquired sample representation of a pulse dispersed by the substance.

According to yet another aspect of the invention, a time-gate function is applied to a response signal arising from the interaction of the substance with pulses of energy to accept energy in the response signal that arrives at a receiver only during one or more specified time intervals to discriminate against unwanted portions of the response signal.

According to another aspect of the present invention, the pulses received by the receiver may be displayed on a suitable visual display, showing the amplitude and shape of the received pulses as a function of time. A time lag between the time when a pulse is transmitted and the time when the pulse is received is caused by the time duration of propagation of the pulse interacting with the material. This time delay can be visually observed and employed to infer properties of the substance. Further, the material interacting with the pulses may cause an attenuation of pulse amplitude that can also be visually observed. Moreover, the substance interacting with the pulses may cause dispersion of the pulses, thereby causing a visibly observable distortion of the shape of the pulses.

According to another aspect of the invention, the received pulses may be processed electronically by digital or analog electronics to obtain information concerning the substance from observables such as propagation delay, attenuation and dispersion. For example, the received pulses may be sampled, converted to a digital information format, and then processed by a computer operating under the directions of software to perform analysis of the received information that yields knowledge of the composition of the substance. Alternatively, the acquired digital information may be transformed to a frequency domain representation and displayed and analyzed as a function of frequency.

The foregoing has outlined rather broadly aspects, features and technical advantages of the present invention in order that the detailed description of the invention that follows may be better understood. Additional aspects, features and advantages of the invention will be described hereinafter. It should be appreciated by those skilled in the art that the disclosure provided herein may be readily utilized as a basis for modifying or designing other structures for carrying out the same purposes of the present invention. Persons of skill in the art will realize that such equivalent constructions do not depart from the spirit and scope of the invention as set forth in the appended claims, and that not all objects attainable by the present invention need be attained in each and every embodiment that falls within the scope of the appended claims.

BRIEF DESCRIPTION OF THE DRAWINGS

For a more complete understanding of the present invention, and the advantages thereof, reference is now made to the following descriptions taken in conjunction with the accompanying drawings, in which:

FIG. 6 is a block diagram of another embodiment of the present invention suitable for conveyor belt applications and the like.

DETAILED DESCRIPTION OF THE PREFERRED EMBODIMENTS

Figure 5:
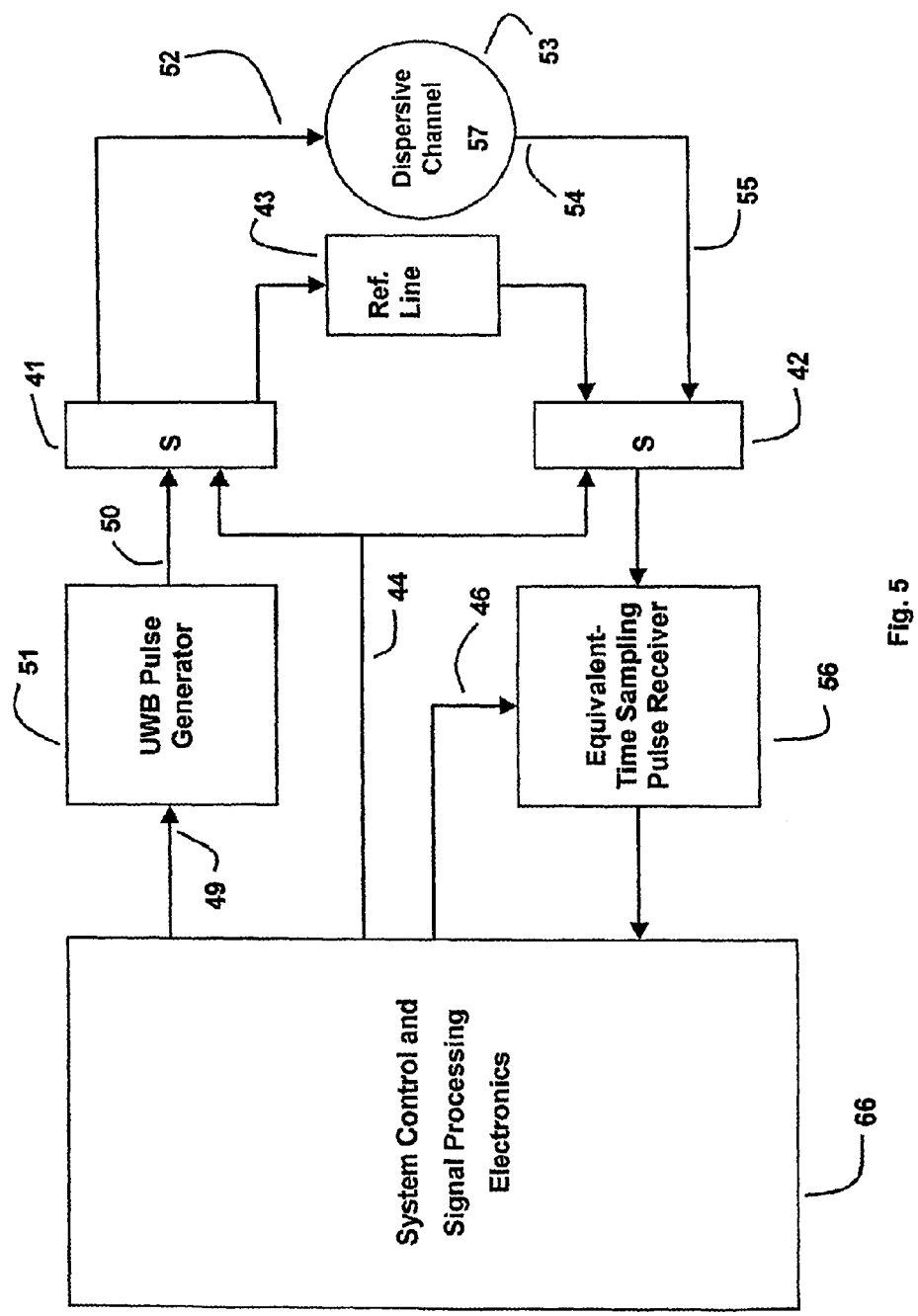
FIG. 5 is a block diagram of an embodiment of the present invention.

A preferred embodiment of the present invention is shown in FIG. 5. FIG. 5 shows an Ultra-Wide-Band (UWB) pulse generator 51, comprising UWB pulse generation circuitry for generating a repetitive sequence of Ultra-Wide Band energy pulses at output 50. Each pulse in the sequence is similar to the single pulse shown in FIG. 1. These pulses are communicated, through a switch 41, to the input port at 52 of a measurement cell 53 that contains a material 57 to be tested. The loaded measurement cell forms a dispersive propagation path that transforms the received energy to produce a response signal comprising a sequence of modified output pulses at 55. The response signal is communicated, through a switch 42, from an output port at 54 to an equivalent time sampling pulse receiver 56. The pulse receiver 56 samples the response signal to produce an acquired sample representation that is analyzed by processing and control electronics 66 to determine material parameters of interest.

Measurement cell 53 may be simply a section of pipe within the industrial process containing the substance, or may be a specially constructed wave-guide or other structure through which the material is caused to pass. The input port 52, through which the pulsed energy is transmitted to cell 53, typically comprises or incorporates a probe, loop, aperture or other transmitting element (not shown) that couples the pulse energy into measurement cell 53. The electromagnetic fields inside the dispersive measurement cell 53 propagate and are distributed therein according to Maxwell's equations. These fields excite a receiving element (not shown), similar to the input transmitting element, at output port 54. The receiving element functions to couple a portion of the electromagnetic energy in cell 53 through output port 54 to produce the sequence of output pulses 55.

Figure 1:
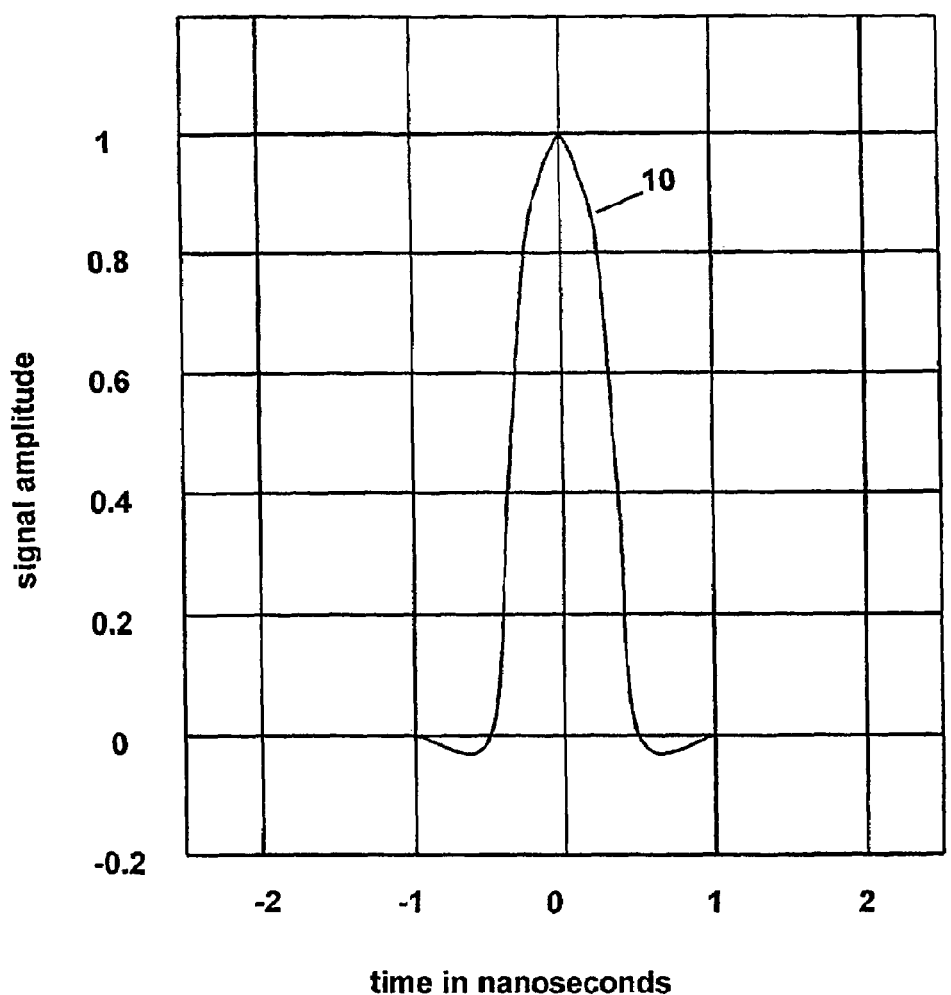
FIG. 1 is a graphical representation of a typical ultra wide-band pulse signal.

The pulses generated by pulse generator 51 are of short duration. The particular pulse shown in FIG. 1 is a Gaussian amplitude-weighted sin(x) over x pulse, representative of a general class of UWB pulses, but not the only type of pulse that may be employed in the present invention. (Note that in FIGS. 1 and 4, both negative and positive values appear along the horizontal axes as shown, with time t=0 coinciding with the peak of the pulse. This is consistent with standard mathematical analysis methods, although other coordinate orientations can be employed.)

An inverse relationship exists between the time duration of a pulse of energy and the frequency bandwidth of the energy spectrum of the pulse. The shorter the duration of the pulse, the wider will be the band of frequencies of energy comprising the pulse. Therefore, the frequency spectrum of a narrow input pulse, such as is shown in FIG. 1, will resemble the broad spectrum shown in FIG. 2. Thus, a sufficiently narrow UWB pulse will exhibit a broad frequency spectrum of energy that interacts with the substance over a desired frequency range to which the substance is responsive to the interacting energy.

Because the energy coupled to measurement cell 53 exhibits a broad frequency spectrum, the energy distribution in measurement cell 53 will also exhibit a broad frequency spectrum. This broadband energy distribution in the cell interacts with, and is dispersed by, the material. This dispersion is a function of frequency, the shape and size of the cell, and of the characteristics of the material.

Figure 3:
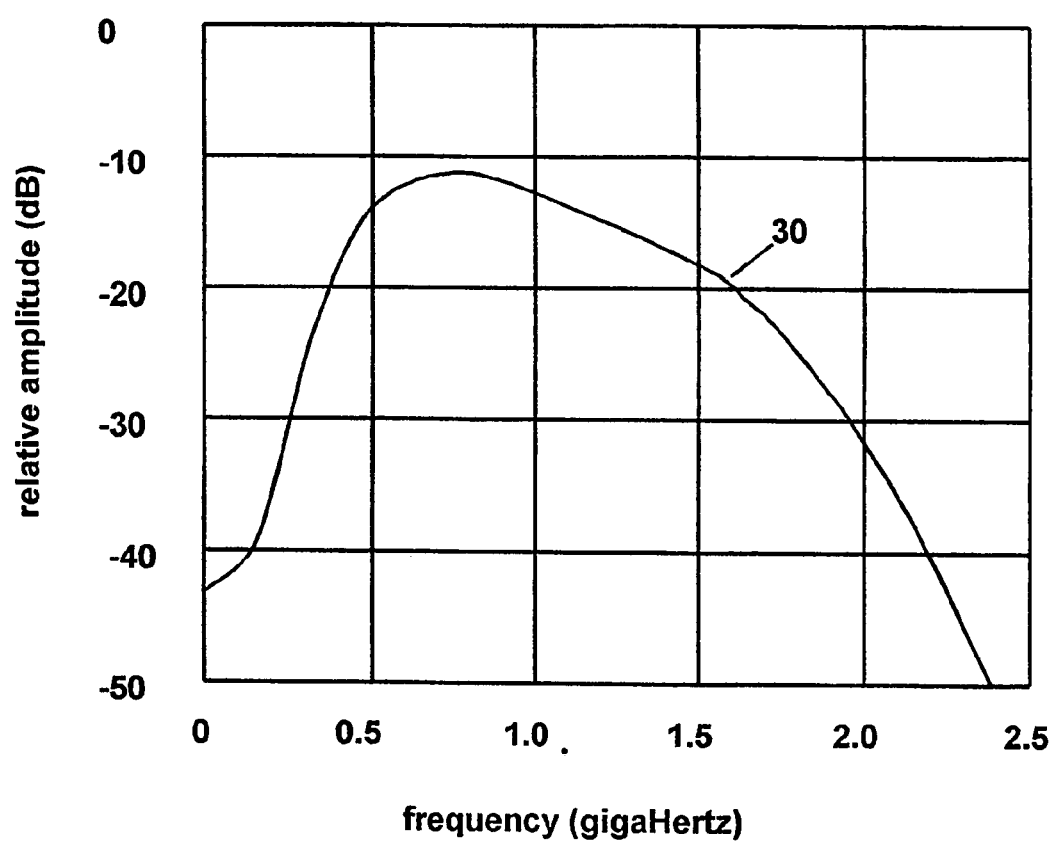
FIG. 3 is the frequency domain representation of a transfer function of a dispersive transmission channel through which the signal of FIG. 1 has traveled.
Figure 4:
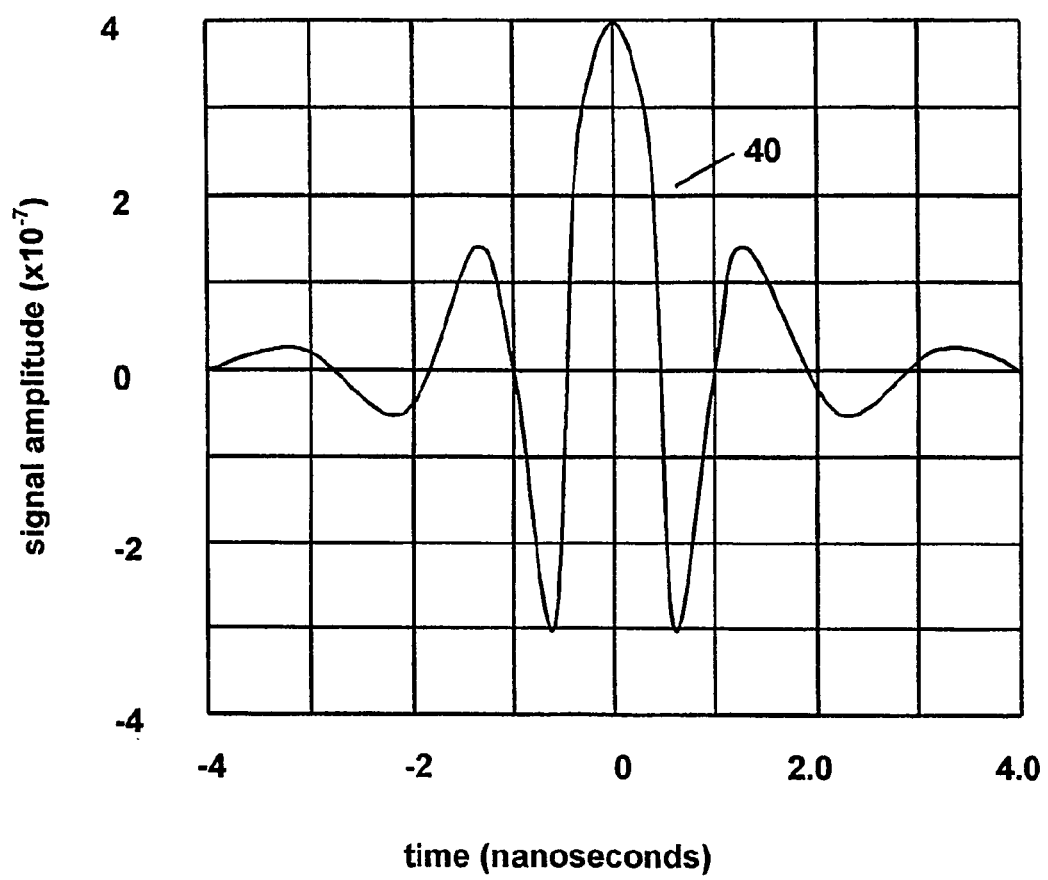
FIG. 4 depicts a time domain representation of the signal of FIG. 1 after it has been distorted by having transited a dispersive channel according to the present invention.

Dispersion affects the shape, duration, phase and time of arrival of the energy pulses coupled to the sampling pulse receiver. Thus, measurement cell 53 and the substance therein forms a dispersive channel with a frequency response of substantial amplitude over a broad spectrum. An illustrative response that may be exhibited by a dispersive channel formed by measurement cell 53 and a substance there within, is shown in FIG. 3. The effect of such a dispersive response upon an input pulse is shown in FIG. 4, which illustrates a typical one of the output pulses 55. The input pulse waveform 50 will therefore be modified by the dispersive characteristics of the measurement cell and the substance. Consequently, the output waveform 55 contains information enabling characterization of the substance 57.

As noted, the output pulse signal 55 is coupled through a switch 42 to an equivalent time sampling pulse receiver 56. Receiver 56 samples the received signal, preferably according to an equivalent-time sampling technique that is typical of wide bandwidth sampling oscilloscopes such as, for example, a Tektronix S4 74S11 74T11 with a 7000 series mainframe, a Tektronix 11801B with SD22 sampling head, or a Hewlett Packard 54120 series oscilloscope. This same equivalent-time sampling method is employed in currently available, low-cost pulse radar level gauges. As is the case for the level gauging radars, the use of the equivalent-time sampling method in the present invention allows low cost implementation for the electronics at the output of the receiver because it permits the use of a low cost analog-to-digital converter.

More specifically, in a preferred embodiment, output pulses 55 received by sampling pulse receiver 56 are time-sampled to convert them to a digital format that can be used by processing electronics 66. To form an accurate digital representation of a narrow-width pulse would ordinarily require that the pulse be sampled at a very high sampling rate, which requires relatively costly electronics. This high cost can be avoided using the equivalent-time sampling technique. Rather than sample each pulse at a very high rate, each sample needed to provide an accurate representation of a pulse is acquired from a different pulse in the sequence of pulses 55 received from measurement cell 53. This allows use of a much slower sampling rate because of the relatively long time duration between pulses. The samples obtained from each pulse are then temporally aggregated to form an acquired sample representation that accurately reproduces a dispersed pulse. This sampling method substantially reduces the cost of the pulse receiver and enables the advantageous use of ultra-wide band pulses for material measurements that would otherwise be prohibitively expensive in many applications.

After collecting a sufficient number of samples from the output pulse sequence, a reconstructed equivalent-time sampled pulse will be produced by receiver 56 that has the basic shape of the distorted pulse signal 40 shown in FIG. 4. A sufficient number of samples depends upon the amount of dispersion in the measurement cell and upon the amount of averaging that is required to produce a representative signal. These factors will vary from application to application and will best be determined by experience.

Because energy propagates in the apparatus, unwanted reflections of propagating energy from obstructions exterior to the measurement cell can occur. However, because of the time delay that occurs for propagating energy to exit the measurement cell, reflect from an obstruction, and return to the measurement cell, this unwanted reflected energy will arrive at a time that is discernibly later than the time of arrival of the dispersed energy pulse that is communicated directly through the measurement cell. The sampling pulse receiver can therefore discriminate between the late-arriving energy and the pulsed energy communicated directly through the cell. By excluding the late arriving energy from the process, measurement errors arising from unwanted reflections are avoided.

To accurately measure time of arrival and the dispersion caused by the material, as well as to distinguish the dispersed pulse from unwanted later-arriving energy, the ultra-wide band pulses must be of very short duration, preferably exhibiting a very rapid rise time, and the time duration between successive pulses must be sufficiently long in comparison to the duration of a pulse. For a typical application, the duration of a pulse is less than a nano-second and the Pulse Repetition Frequency (PRF) is on the order of a few Mega-Hertz (MHz).

The timing of the pulses in the repetitive sequence can be at a regular spacing according to a fixed pulse repetition frequency. That is, the time intervals between successive pulses will all be substantially equal. Alternatively, a pseudo-random or other non-uniform pulse spacing technique can be used. A non-uniform spacing can be selected that will distribute the various frequency components in the pulse sequence over a broad band of frequencies which will appear as a low level noise spectrum to other electronic equipment that could otherwise be affected by stray emissions from the sensor electronics.

Once the acquired sample representation of the dispersed pulse is obtained, it may be directly analyzed by the processing electronics. Further, the dispersed energy pulses sampled by the receiver can be analyzed by comparison to the amplitude and timing of the input pulses, which is communicated from pulse generator 51 through switch 41, through a reference line 43, and through switch 42 to receiver 56, to determine material parameters of interest.

Also, the acquired sample representations may be displayed on a visual display device, such as a video monitor, and visually observed to obtain information concerning properties of the substance. For example the visual display may show the amplitude and shape of the received pulses as a function of time. A time lag between the time when a pulse is transmitted and the time when the pulse is received is caused by the time duration of propagation of the pulse interacting with the material. This time delay can be visually observed and employed to infer properties of the substance. Further, the material interacting with the pulses may cause an attenuation of pulse amplitude that can also be visually observed. Moreover, the substance interacting with the pulses may cause dispersion of the pulses, thereby causing a visibly observable distortion of the shape of the pulses.

Those skilled in the art will recognize that the output signal can be visually display and analyzed in either the time or frequency domain. A signal that varies as a function of time may be represented by a unique signal that varies as a function of frequency. Either representation contains equivalent information. They are mathematically related by the Fourier Transform integral. This integral resolves a continuous-time signal into a continuous-frequency spectrum. Thus, in the alternative to time-domain analysis, it may be convenient to convert the output equivalent-time sampled pulse signal to the frequency domain. The acquired sample representation may be converted to a frequency-domain representation using a Fast Fourier Transform (FFT) algorithm prior to further analysis. The FFT resolves the acquired sample representation into a discrete frequency spectrum.

In the embodiment shown in FIG. 5, depending on the physical dimensions and geometry of the cell, as well as the characteristics of the substance, energy below a certain frequency may be unable to propagate, exhibiting only attenuation, whereas energy above that cutoff frequency will propagate in a wave-like manner. Thus, when the UWB pulses are applied to measurement cell 53, propagating energy will be excited in the cell simultaneously with any non-propagating energy modes that may exist. By converting the acquired sample representation to a frequency-domain representation, the cutoff characteristics may be observed to provide an additional or alternative mode of substance characterization.

Figure 2:
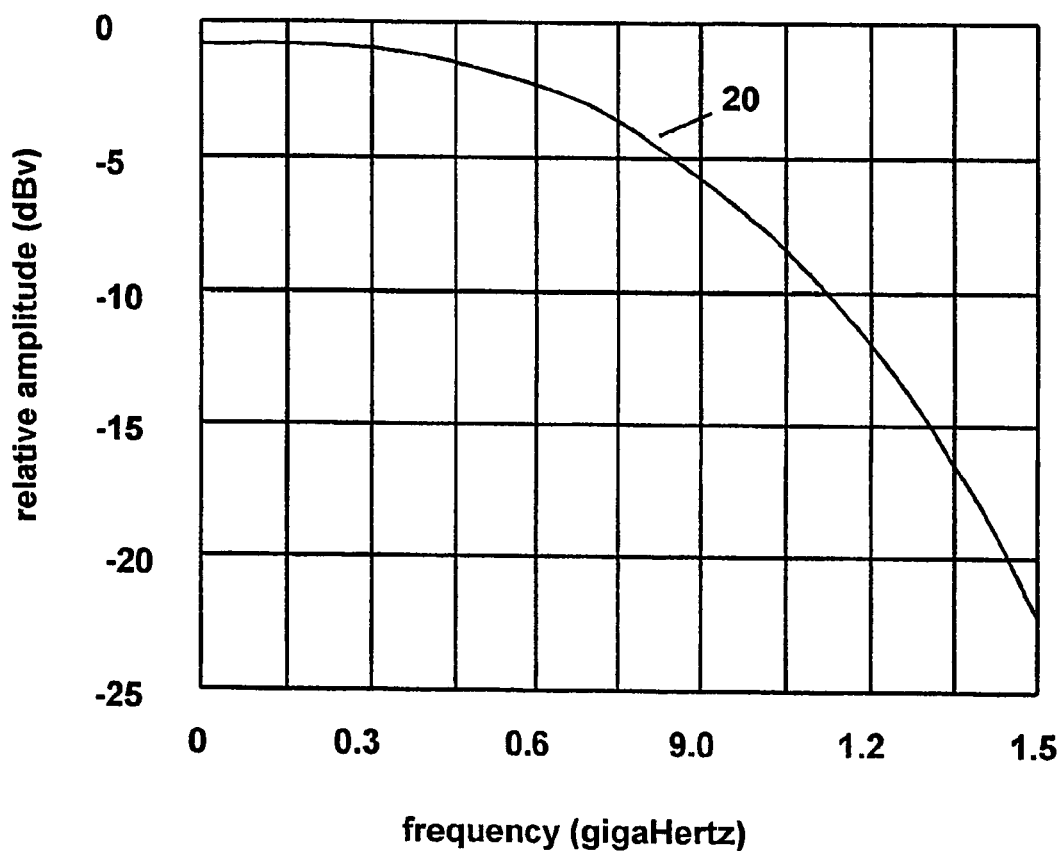
FIG. 2 is the frequency domain representation of the pulse in FIG. 1.

FIG. 2 is the Fourier transform or frequency domain representation 20 of the pulse 10 shown in FIG. 1. The frequency domain representation 20 shows the wide bandwidth characteristics of the signal. The transfer function of the dispersive channel, which is the output response of the channel to an impulse, is shown in FIG. 3. The output pulse 40 is shown in FIG. 4. In the frequency domain it is generally easier to observe the effects of the dispersion caused by the measurement cell transmission characteristics. For example, one can observe from the spectrum 30 shown in FIG. 3 that the output pulse 40, unlike the input pulse 10, will have substantially no dc component. The removal of the dc component is caused by the high pass filter characteristic of the measurement cell 53, as illustrated in FIG. 3.

The cell 53 will typically have a cutoff frequency characteristic such that frequencies below a certain value experience a large increase in attenuation. The dimensions of the measurement cell 53 and the real part of the permittivity determine the cutoff frequency value. By Fourier-transforming the output pulse, the high frequency attenuation characteristic of the channel is revealed, providing high frequency loss characteristics of the material under test.

It will often be useful to normalize the spectrum of the output pulse by the spectrum of the input pulse. The normalization process has the benefit of removing unit-to-unit variations in both the amplitude of the transmitted pulse and the gain and frequency response characteristics of the receiver electronics 56. To accomplish the normalization, an attenuated sample of the transmitted pulse may be applied directly to the input of the receiver 56 through reference line 43. The receiver electronics 56 are then used to reproduce an equivalent-time sampled version of the transmitted pulse. A Fast Fourier Transform (FFT) operation can then be performed to produce a spectral representation of that pulse. When the Fourier-transformed attenuated transmit pulse and the Fourier-Transformed output signal are converted to deci-Bels (dB), normalization involves simple subtraction operations. In contrast, normalization in the time domain would involve an inverse convolution, which is computationally intensive by comparison.

Depending upon the size of the measurement cell 53, several waveguide modes may be excited by the input pulse 10. The frequency domain representation of the signal will show the location of the cutoff frequencies of the various higher order modes that are excited. The location of these modes is additional information about the frequency dependence of the permittivity of the material under test 57. A sufficiently narrow UWB pulse will exhibit a broad frequency spectrum of energy that excites both propagating modes and non-propagating modes in applications where a measurement cell exhibits cutoff characteristics used to provide information concerning the composition of the substance.

Therefore, if the dispersed UWB pulse collected by the receiver is analyzed in the frequency domain, the spectrum of the pulse, after being normalized to the spectrum of the input pulse, will yield a signature of the material filling the pipe that is analogous to that produced by a sensor that sweeps in frequency to measure the system's spectral response. Thus, in the present invention, a simple UWB pulse transceiver replaces the complex, slow, and costly scalar network analyzer system required for the Guided Wave Spectrometer (GMS) method of the prior art.

Further, although applying a Fourier Transform to the output signal enables display and analysis in the frequency domain, other transformations may be applied to the signal captured by receiver 56 to cause other attributes of the signal to be exhibited and analyzed. For example, certain frequency components may be weighted more heavily due to a priori knowledge concerning a desired frequency response of the substance. Likewise, the acquired signal may be time-weighted to emphasize certain temporal features of the signal. As another example, the acquired signal, after being transformed to the frequency domain may be processed by digital filtering before further analysis. Also, the signal can simply be integrated or differentiated prior to or after one or more other transformations are applied. Thus, more generally, the response signal may be processed by performing a transformation of the response signal to produce a resultant signal that is a function of a variable of the transformation.

The aforementioned signal processing of the acquired sample representation obtained in receiver 56 are performed by processing and control electronics 66. Thus; the signal acquired in the receiver is transferred to processing and control electronics 66 where further processing occurs. Within the electronics 66, decision algorithms predict values for the parameter variables of interest, such as, for example moisture content. As will be understood, electronics 66 may comprise a microprocessor operating under the directions of software that implements the desired algorithms and other functions.

The functions performed by electronics 66 also comprise system-timing operations, including pulse initiation 49 for control of pulse generation by pulse generator 51, generating switch control signals 44 for control of switches 41 and 42, receiver sampling control 46 for control of sample timing in receiver 56, as well as synchronization and interactive system and visual display control.

To initiate a measurement according to an embodiment as described with reference to FIG. 5, an UWB pulse is launched into a pipe or other wave-guiding structure containing the material under test. The pulse energy transits a known distance through the material and is subsequently received by a receiving probe or aperture. The transit path may be one-way or two-way, depending upon whether the sensor is configured for measuring transmission or reflection, respectively. The dispersive nature of the transmission path within the pipe or waveguide will alter the shape and phase of the UWB pulse according to the dimensions of the pipe or waveguide and the electrical properties of the material under test.

The resultant output signal will have multidimensional information. The amplitude of the received pulse will contain loss factor information related to conductivity. The low frequency portion of the spectrum will contain information on the real part of the complex electrical permittivity. The high frequency portion of the spectrum will provide information related to the high frequency loss components, due primarily to molecular rotation effects.

A major advantage of the present invention is provided by the time-domain gating employed in receiving and processing the UWB pulses. The process of time gating comprises excluding energy in the received signal that occurs before or after a designated time. This gating eliminates the frequent sources of error in many industrial applications arising from the upstream and downstream reflections of energy from obstructions exterior to the measurement cell.

When a pulse is communicated to the substance, energy from the pulse passing directly through the substance will arrive at the receiver before the arrival of energy from the pulse that exits the measurement cell and reflects from an obstruction before returning to the measurement cell to be coupled through output port 54. Therefore, by accepting energy during a time when the directly communicated pulse energy arrives at the receiver and excluding energy during a time when the later-arriving pulse energy arrives, the late arriving energy is excluded from the measurement.

Thus, a time-gate functions to exclude energy in the signal that does not arrive at the receiver during a specified time interval. When the pulse generator produces a repeating sequence of pulses the time gate is applied repetitively to exclude unwanted energy arising from each pulse in the signal, while accepting the desired energy arising from each pulse.

To avoid the aforementioned unwanted reflections, the GMS method of the prior art employed a costly rectangular waveguide section, with round-to-rectangular transition sections to convert the circular process pipe cross section to the rectangular cross section of the guide. The excitation signal was then transmitted transverse to the flow of the substance through the waveguide to substantially prevent wave propagation in the process pipe exterior to the waveguide.

Time gating eliminates the need for implementing this costly and sometimes impracticable configuration. Time gating enables the employment of a section of circular process piping as the wave guiding structure, while allowing signals to travel up and down the length of the pipe without interfering with the measurement process. Time gating also greatly expands the range of applications for composition analysis since a much wider range of pipe sizes can be accommodated. The invention thereby satisfies an important need within the process industry.

Alternatively, the present invention may utilize the rectangular sections described above in reference to the GMS method, and transmit UWB pulses across the waveguide, without departing from the scope or the novelty of the UWB pulse dispersion spectrometry method described herein. Many variations of the basic measurement cell are contemplated, all of which will provide a dispersive signal path that is influenced by the properties of a material under test 57.

Figure 6:
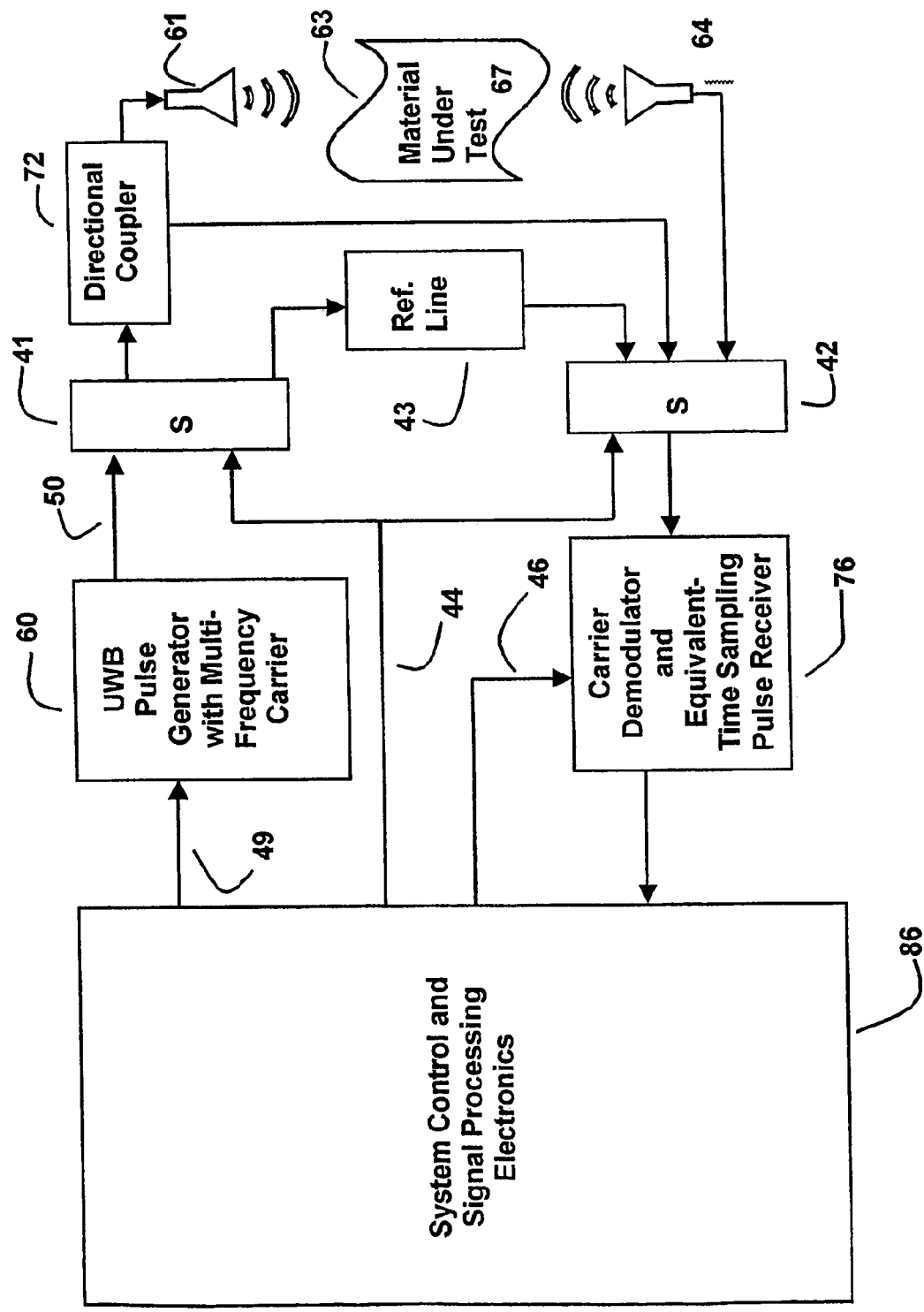

Another embodiment of the invention that constitutes a novel application of UWB pulse energy and a dispersive transmission channel is that of an instrument suited for conveyor belt applications, as shown in FIG. 6. A pulse transmitting circuit 60 generates an UWB pulse, or a sequence of UWB pulses at 50. These pulses typically are modulated on a carrier signal selected from a set of known frequencies. Modulation of the pulses by a carrier frequency enables radiation of the energy pulses by an antenna of suitable dimensions. These pulses are then communicated through a switch 41 and directional coupler 72 to an antenna 61. Antenna 61 radiates the pulsed energy toward the material under test 67, which is supported by a supporting structure 63 such as, for example, a conveyor belt in an industrial process. Because the pulses generated by pulse generator 60 are narrow, the average power of the carrier-modulated signal radiated by antenna 61 will be relatively low.

The supporting structure does not confine the energy radiated by antenna 61, so that some of the radiated energy is transmitted through the material and some of the energy is scattered by, and away from, the material. Thus, antenna 61 may also be positioned to receive some of the pulsed energy that is scattered by the material. In this configuration, antenna 61 is both a transmitting element and a receiving element. These received energy pulses are coupled through the directional coupler 72 to the sampling pulse receiver 76, which comprises a carrier demodulator. Receiver 76 produces an acquired sample representation, as described above. This data is then processed by the processing electronics 86 to obtain information concerning the shape and thickness of the material.

Antenna 64 is positioned to receive pulsed energy that is transmitted through, and dispersed by, the material under test. These received pulses are coupled to the sampling pulse receiver 76 to produce an acquired sample representation, which is processed in electronics 86 to determine material properties of interest.

Thus, antenna 61 may be positioned above a conveyor belt carrying a substance to be tested and antenna 64 may be positioned below the conveyor belt. The material under test, because of its frequency dependent electrical properties, constitutes a dispersive transmission path for the UWB pulse energy. An irregular surface and non-homogeneous distribution of the material on the belt may also contribute to dispersion.

A first signal is reflected and scattered from the surface of the material covering the belt and is collected by the first antenna 61. The time of arrival of this first received pulse will be dependent upon the thickness of the material on the belt. The width of the received pulse will be a function of the shape of the surface of the material.

A second signal is transmitted through the material on the belt and is received by the second antenna 64. This second received pulse will be distorted by having traveled through the material under test 62 and will be delayed and attenuated. The amount of time delay and the amount of attenuation will be a function of the electrical properties of the material through which it must pass to reach the second antenna.

The signal acquired by the receiver is then transferred to processing and control electronics 86. Within the electronics 86, decision algorithms predict values for the parameter variables of interest, such as, for example moisture content. Electronics 86 may comprise a microprocessor operating under the directions of software that implements the desired algorithms and other signal processing, control and timing functions as discussed above with reference to the embodiment of FIG. 5.

Note that the signal received by antenna 61, denoted above as the first signal, may be received before or after the signal received by antenna 64, which is denoted above as the second signal. The relative timing of the first and second signals can be controlled by the cabling used to connect the first and second antennas to their respective receiver ports and upon the positioning of these antennas with respect to the material being interrogated.

Note also, that the reflected signal received by antenna 61 could be used to measure the level of the material surface in a manner similar to other level gauging radars, but according to the present invention no computation of distance from antenna 61 to the surface of the substance is required. Instead the time of reception of the signal received by antenna 61 serves as a reference time to which the arrival time of the signal received by antenna 64 is compared. This is discussed more fully below with reference to FIG. 7.

The accuracy and flexibility of measurement algorithms will often be enhanced by the use of multiple carrier frequencies. Although the use of multiple carrier frequencies will increase the cost of the instrument, the added dimensionality of the signals may prove necessary or beneficial for some applications.

Figure 7:
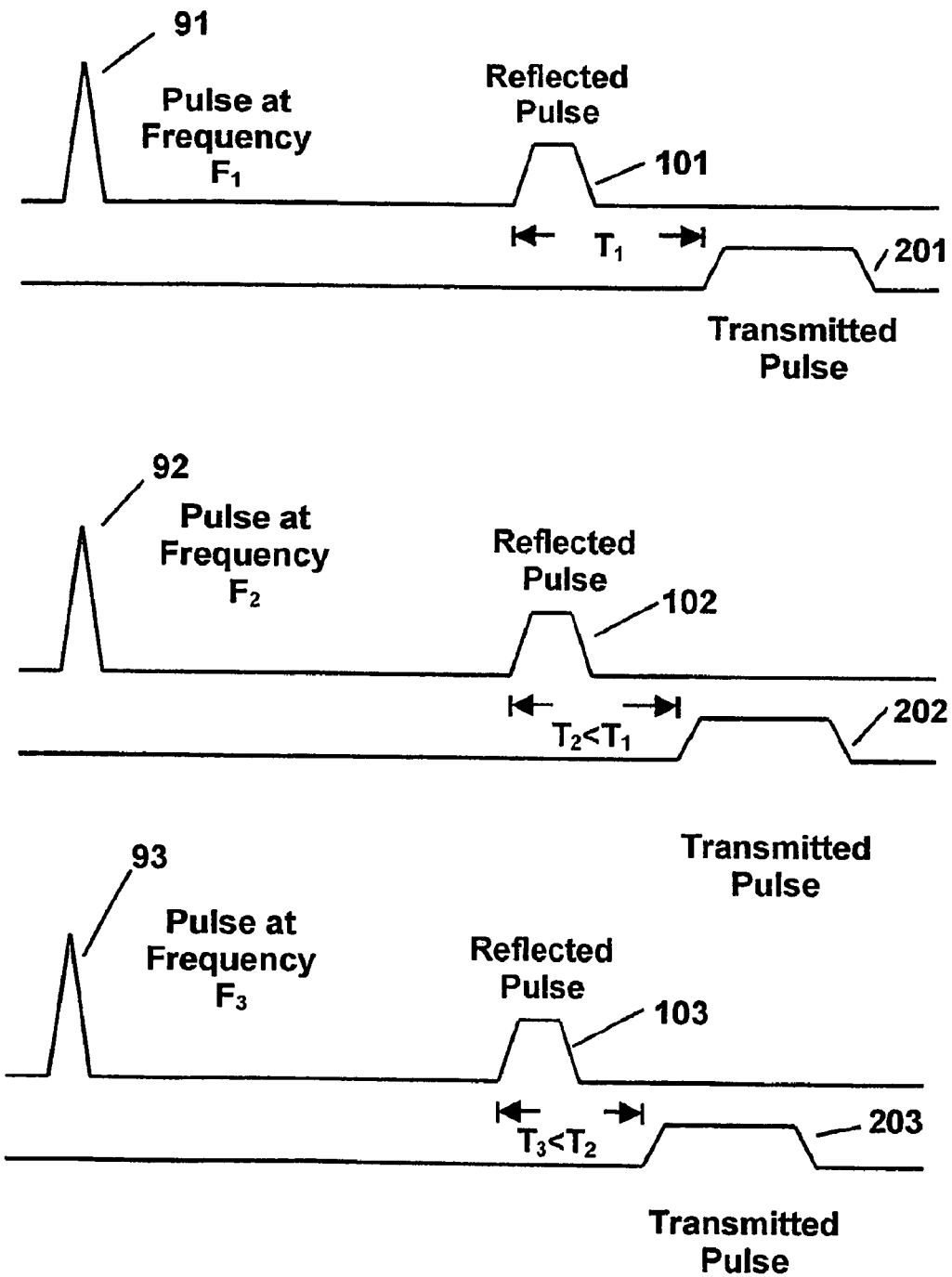
FIG. 7 illustrates the relative timing of pulses that are transmitted at different modulation frequencies.

FIG. 7 illustrates one set of measurements employing UWB pulses 91, 92, and 93, each modulated onto carrier signals at three distinct frequencies, F1, F2, and F3, respectively. The order in which the frequencies are transmitted is of no particular relevance for the measurement set contemplated. We will assume that frequency F3 is higher than frequency F2, which is, in turn, higher than frequency F1. For each element of the set, the waveforms represent the equivalent-time sampled signal after the carrier frequency has been removed. The respective reflected pulse waveform 101, 102, and 103, is produced by a signal having arrived at the input of the receiver after being reflected from the substance. The respective transmitted pulse waveform 201, 202, and 203, represents the result of a signal having been transmitted through the material under test.

The velocity of propagation of the pulse energy through the material under test will be different for each carrier frequency due to the frequency dependent nature of the electrical properties of the material being measured. The time of flight of the transmitted pulse, referenced to the time of the reflected pulse, will therefore be different for each carrier frequency. Thus, for the situation described here, the time of flight T1, corresponding to frequency F1, will be greater than the time of flight T2, corresponding to frequency F2, which is in turn greater than the time of flight T3, corresponding to frequency F3.

Clearly, the waveforms of FIG. 7 are idealized signal representations and do not illustrate all of the various features of real signals that arise from the interactions of the reflected and transmitted pulses with the substance at the different carrier frequencies. Thus, the composite effects of the many variables affecting a conveyor belt measurement will be such that an idealize set of signals as shown in FIG. 7 will not be produced. However, the general behavior as depicted for the time of flight through the material under test will indeed be exhibited by real signals. Also, the relative time position of the reflected pulse and the transmitted pulse need not be such that the reflected pulse arrives earlier in time than the transmitted pulse. The relative timing of these pulses will depend upon antenna position and upon the lengths of cable connecting the antennas to the sensor electronics.

What the idealized signals of FIG. 7 illustrate is how the dispersive characteristic of the material under test will affect the time of travel for each frequency as it passes through the material. The difference in time of flight as a function of carrier frequency enhances the ability to extract multiple component analysis information from the set of signals. Prior art time-of-flight methods for composition analysis consider only the propagation delay and depend upon non-dispersive paths. In the present invention, a dispersive path is desired so as to encode composition information into the distortion characteristics of the pulse.

Thus, the second embodiment of the present invention, described above with reference to FIG. 6, is useful for analyzing the properties of materials that are not contained in a pipe or waveguide structure, such as materials on a conveyor belt. For instance, it is often desirable to measure the moisture content of a granular material being conveyed on a belt. Several configurations for microwave sensors have been proposed in the past, but all of the proposed systems have fallen short of general practical use.

For example, EG&G Berthold has offered a system that measures the properties of a continuous microwave signal at several frequencies passing through a material on a conveyor belt. Since material thickness and density can vary widely, a simple attenuation and phase shift measurement, even at multiple frequencies, is not sufficient to provide reliable moisture measurement. The Berthold system adds a gamma ray sensor to provide an independent measurement to help account for the unknown variables, but the cost of such systems quickly becomes prohibitive.

In addition to time of flight measurements, pulse duration of the reflected signal is also analyzed to augment time of flight measurements. These signal attributes, like the attributes of signal associated with the embodiment described with reference to FIG. 5, will serve as input parameters that decision and analysis software in processing electronics 67 will process to yield a calibrated estimate of the material property desired to be known by the user. Experience will dictate whether the various signal attributes are best represented in the time or frequency domains. Those skilled in the art will appreciate the various tradeoffs that are presented for the extraction of the signal parameters that provide a simple and robust signal measurement space.

Thus, according to the embodiment of FIG. 6, the present invention makes novel use of UWB radar technology and the dispersive velocity characteristics induced by a substance to provide a simple and low cost solution to this vexing problem. A UWB pulse is modulated onto one or more carrier signals whose frequencies are selectable from a known set of frequencies. Each selected frequency provides for an independent measurement of the height of the product and the time-of-flight delay for the signals traveling through the material.

Conveniently, carrier frequencies designated for the so-called ISM bands may be selected to mitigate interference issues and to possibly comply more easily with any applicable FCC regulations.

The time of flight through the material will be different at each carrier frequency, based upon the frequency dependent characteristic of the electrical permittivity, which, for moisture content measurements, is strongly influenced by the electrical properties of water. By analyzing attenuation and time delay measurements, optionally at multiple frequencies, moisture content of the material on the belt can be readily measured without the need for additional sensors.

A timing signal reflected from the surface of the material on the belt will enable the sensor to compensate for differences in thickness, while the multi-dimensional nature of the attenuation and time delay measurements at each of the frequencies in the measurement set will enable the sensor to make a measurement, such as moisture content, that is independent of material density as well.

For both the enclosed embodiment of FIG. 5 and the open-space embodiment of FIG. 6, there are various mathematical operations that can be performed on the received pulse signals that may aid in the extraction of the information encoded in the pulse energy after it has been influenced by the dispersive properties of the substance. Also, there is a large body of available software analysis tools that can be employed to extract the information that is inherent in the signals.

For example, there are various regression methods and principal component analysis methods that are well known by those skilled in the art as being useful for calibrating such sensors to the variable or variables of interest. For example, see the book *Multivariate Calibration* by Harald Martens and Tormod Nægs, published by John Wiley and Sons.

Thus, the systems of the present invention may be calibrated by observing the process involving the substance over a range of known operating conditions and collecting data associated with those conditions. Such conditions may comprise temperature, pressure, flow rate, moisture content, and relative concentrations of component materials. The collected data may be analyzed to produce calibration information concerning the response of the system under a set of known operating conditions. This calibration information may comprise mathematical operations, equations, or simply stored data that is derived from the observations of known conditions. The calibration information may then be used to predict or estimate the conditions that exist when the operating conditions are unknown. Thus, information obtained during observation of the process involving the substance may be compared to the calibration information to ascertain the operating conditions existing during the current observations.

Figure 8:
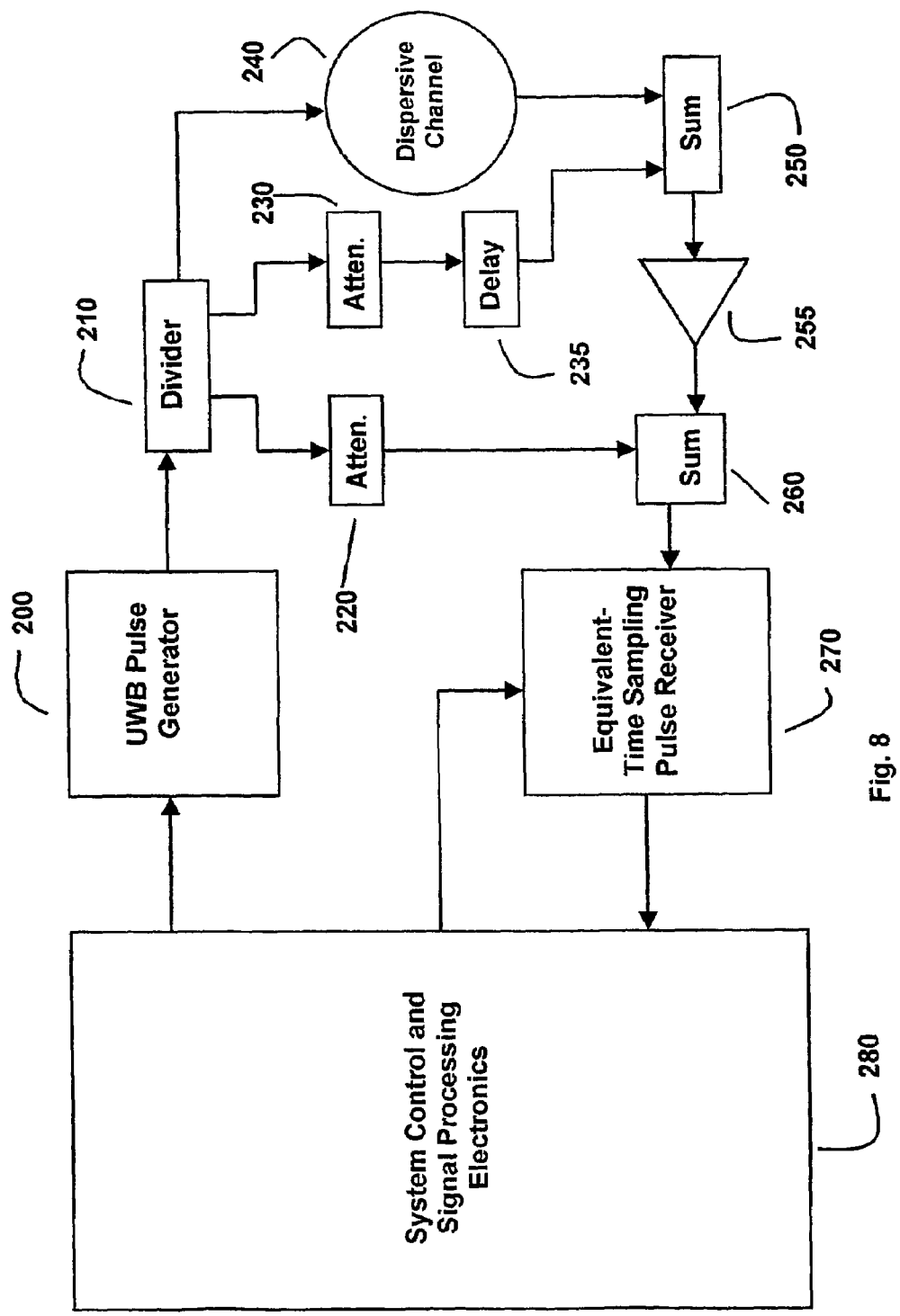
FIG. 8 illustrates a block diagram of an embodiment of the present invention.

Another embodiment of the present invention is shown in FIG. 8. Here, pulse generator 200 sends a pulsed signal to a divider 210. Divider 210 sends the pulsed signal to a first attenuator 220, a second attenuator 230, and to the dispersive channel 240. Dispersive channel 240 contains the substance to be analyzed. The pulsed signal propagates through channel 240 and is coupled to a summing network 250.

The pulsed signal coupled to attenuator 230 is attenuated by attenuator 230 and sent to a delay device 235. Delay device 235 delays the attenuated pulsed signal from attenuator 230. The delayed attenuated pulsed signal from delay device 235 is coupled to summing network 250. There, the delayed attenuated pulsed signal is summed with the response signal received from dispersive channel 240. The output of summing network 250 is input to an amplifier 250. Amplifier 250 amplifies the input signal and couples the amplified signal to a second summing network 260.

The pulsed signal coupled to attenuator 220 is attenuated by attenuator 220 and sent to summing network 260. The signal received from attenuator 220 and the signal received from amplifier 255 are summed in summing network 260. The summation signal output from summing network 260 is coupled to the input of an equivalent-time sampling receiver 270.

Receiver 270 operates as described above with respect to receiver 56 to provide an acquired sample representation to processing electronics 280, which performs the functions described above with respect to processing electronics 66, including providing a sampling control signal to receiver 270. However, the switch control signal 44 provided by processing electronics 66 in the embodiment of FIG. 5 is not necessary to be provided in the embodiment of FIG. 8.

As mentioned, when a pulse in the pulsed signal generated by pulse generator 200 is transmitted to divider 210, it is sent to attenuator 220, attenuator 230 and channel 240. Let the pulse passing through attenuator 220 be denoted as pulse A. Let the pulse passing through attenuator 230 be denoted as pulse B. And, let the pulse passing through dispersive channel 240 be denoted as pulse C. Then, the system of FIG. 8 is preferably configured as follows: pulse A arrives at summer 260 before the combination of pulse B and pulse C arrives at summer 260 from amplifier 255; and pulse B arrives at summer 250 before pulse C. Consequently, pulse A arrives at receiver 270 before pulse B, and pulse B arrives at receiver 270 before pulse C.

Since the pulses A, B and C arrive at receiver 270 sequentially their power levels upon arrival can be evaluated individually and compared. This enables automatic gain control as will now be explained. Suppose that because of a small amount of attenuation provided by attenuator 220, the power of pulse A at receiver 270 is $P_A$ in dB. Suppose that because of a relatively larger amount of attenuation provided by attenuator 230, the power of pulse B at receiver 270 is the product of G plus $P_B$ in dB, where G is the gain of amplifier 255. Further, suppose that because of attenuation provided by dispersive channel 240, the power of pulse C at receiver 270 is G plus $P_C$ in dB, where again, G is the gain of amplifier 255.

Clearly, the measurements at receiver 270 of $P_A$, $G+P_B$, and $G+P_C$, enable the gain G of amplifier 255 and the attenuation due to dispersive channel 240 to be determined. Further, by applying a feedback signal to amplifier 255 the gain G can be automatically controlled. Thus, the amplification of the response signal can be measured and controlled by measurement of the gain of amplification of the response signal. Therefore, the present invention provides for automatic gain control in the process of obtaining information concerning the substance.

The present invention therefore discloses methods and apparatus that provide multi-component composition analysis of various mixtures of materials using ultra-wideband (UWB) pulses of electromagnetic energy that are caused to travel a path in which the electrical properties of a material under test create or modify a dispersive characteristic of such path and thereby distort the time or frequency domain representation of the UWB pulse signal.

The analysis provides information relating to changes in the electrical properties of a mixture as the relative concentrations of the mixture's components vary, (e.g., its moisture content). The electrical property most often of interest is the frequency-dependent, complex electrical permittivity, although for some materials, magnetic permeability may also be a factor. The frequency range of interest includes the range of frequencies normally associated with microwave composition analyzers.

An important practical aspect of the present invention is advantageous employment of the well-known extended-time sampling method, in conjunction with UWB pulse generation and receiving methods, in order to provide a very low cost composition measurement sensor and method. However, the pulse dispersion analysis method described here stands on its own as being novel, even without the extended-time sampling technique.

Those skilled in the art will recognize that a higher cost embodiment of the invention can be accomplished by implementing a receiver that is capable of processing the full bandwidth of the UWB signals directly. That is, a receiver can be employed that samples the dispersed pulses at or greater than the Nyquist rate. The present invention includes these methods and embodiments as well as the extended-time sampled methods and embodiments that are described here and are considered to be the preferred embodiments of the invention.

The invention is not limited to the embodiments presented here and persons of ordinary skill in the art will recognize that a specific way of implementing the present invention will depend on factors made apparent by this disclosure. The shape and timing of the UWB pulses, the presence or absence of a carrier frequency, the characteristics of the measurement cell, the size of the process pipe, the frequency response of the process substance, for example, are just some of the factors that may need to be considered when choosing a specific way of implementing the invention.

Thus, although the present invention and its advantages have been described in detail, it should be understood that various changes, substitutions and alterations can be made herein without departing from the spirit and scope of the invention as defined by the appended claims. The invention achieves multiple objectives and because the invention can be used in different applications for different purposes, not every embodiment falling within the scope of the attached claims will achieve every objective.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method using electromagnetic energy for obtaining information concerning composition of a substance, comprising:
   generating an ultra-wide band signal exhibiting a continuous, broad band frequency spectrum extending over a range for which the substance is responsive to electromagnetic energy;
   communicating the ultra-wide band signal to the substance to enable electromagnetic energy to interact with the substance at a continuous multiplicity of frequencies simultaneously;
   acquiring a response signal representative of interaction of the energy of the ultra-wide band signal with the substance; and
   processing the response signal to obtain information concerning the composition of the substance.

2. The method of claim 1, wherein processing the response signal further comprises resolving the response signal into a frequency spectrum to determine information concerning individual ones of simultaneous modes of propagation of energy in the substance.

3. The method of claim 1, wherein the ultra-wide band signal comprises a plurality of successive pulses separated by time intervals and acquisition of the response signal further comprises:
   acquiring a sample from each one of a plurality of pulses in the response signal; and
   temporally aggregating the acquired samples to form an acquired sample pulse representation.

4. The method of claim 1, further comprising applying a time-gate function to accept energy in the response signal that arrives at a receiver of the response signal only during one or more specified time intervals.

5. The method of claim 1, wherein the ultra-wide band signal comprises a plurality of successive pulses wherein the time intervals between successive pulses are not all substantially equal.

6. The method of claim 5, wherein the non-uniform spacing between successive pulses is pseudo-random.

7. The method of claim 1, wherein the response signal comprises:
   a reflected signal arising from energy scattered from the substance; and
   a transmitted signal arising from energy transmitted through the substance.

8. The method of claim 1, further comprising determining information about a composition of the substance by comparing a time of arrival of a pulse in the response signal arising from energy scattered from the substance to a time of arrival of a different pulse in the response signal arising from energy transmitted through the substance.

9. The method of claim 1, further comprising providing gain control by:
   propagating the ultra-wide band signal through a first channel in parallel with the substance;
   propagating the ultra-wide band signal through a second channel comprising a delaying mechanism in parallel with the substance; and
   evaluating the signals received from the first and second channels to generate a gain control signal.

10. An apparatus using electromagnetic energy for determining information concerning composition of a substance, comprising:
    a generator for generating an ultra-wide band signal exhibiting a continuous, broad band frequency spectrum extending over a range for which the substance is responsive to electromagnetic energy;
    a transmitting element for communicating energy in the ultra-wide band signal to the substance to enable electromagnetic energy to interact with the substance at a continuous multiplicity of frequencies simultaneously;
    a receiver for acquiring a response signal representative of interaction of the energy of the ultra-wide band signal with the substance; and
    signal processing electronics for processing the response signal acquired by the receiver to obtain information concerning the composition of the substance.

11. The apparatus of claim 10, further comprising signal processing electronics that performs a transformation of the response signal into a frequency spectrum to determine information concerning individual ones of simultaneous modes of propagation of energy in the substance.

12. The apparatus of claim 10, wherein the ultra-wide band signal comprises a plurality of successive pulses separated by time intervals and wherein the receiver acquires an acquired sample pulse representation by performing steps comprising:
    acquiring a sample from each one of a plurality of the pulses in the response signal; and
    temporally aggregating the acquired samples to form the acquired sample pulse representation.

13. The apparatus of claim 10, wherein energy in the response signal is processed only if the energy arrives at the receiver during one or more specified time intervals.

14. The apparatus of claim 10, wherein a time of arrival of a pulse in the response signal arising from energy scattered from the substance is compared to a time of arrival of a different pulse in the response signal arising from energy transmitted through the substance to determine information about a composition of the substance.

15. The apparatus of claim 10, further comprising:
    a first channel in parallel with the substance through which the ultra-wide band signal is propagated;
    a second channel in parallel with the substance and comprising a delaying mechanism through which the ultra-wide band signal is propagated;
    an amplifier of a response signal with a gain derived from the signals received from the first and second channels.

16. The apparatus of claim 10, wherein the ultra-wide band signal comprises a plurality of successive pulses and wherein the spacing between successive pulses is non-uniform.

17. A method using electromagnetic energy to obtain information concerning composition of a substance, comprising:
    generating an ultra-wide band signal exhibiting a continuous, broad band frequency spectrum extending over a range for which the substance is responsive to electromagnetic energy, the ultra-wide band signal comprising a plurality of successive pulses each having a duration substantially less than a time duration between any successive two of them;
    communicating the ultra-wide band signal to the substance to enable electromagnetic energy to interact with the substance at a continuous multiplicity of frequencies simultaneously;
    acquiring a response signal representative of interaction of the energy of the ultra-wide band signal with the substance, applying a time-gate function is to the response signal to accept energy in the response signal that arrives at a receiver of the response signal only during one or more specified time intervals; and processing the response signal to obtain information concerning the composition of the substance by evaluating a dispersive effect of the substance.

18. The method of claim 17, wherein processing the response signal further comprises comparing a time of arrival of a pulse in the response signal arising from energy scattered from the substance to a time of arrival of a different pulse in the response signal arising from energy transmitted through the substance.

19. The method of claim 17, wherein processing the response signal further comprises performing a transformation of the response signal to produce a resultant signal that is a function of a variable of the transformation.

20. The method of claim 17, wherein acquiring the response signal further comprises acquiring a sample from each of a plurality of pulses in the response signal and temporally aggregating the samples to form an acquired sample representation of a pulse in the response signal.

21. The method of claim 17, further comprising obtaining a gain control measurement by:

propagating the ultra-wide band signal through a first channel in parallel with the substance;

propagating the ultra-wide band signal through a second channel comprising a delaying mechanism in parallel with the substance; and evaluating the signals received from the first and second channels to obtain the gain control measurement.

22. The method of claim 21, wherein the first channel comprises an attenuation.

23. The method of claim 17, wherein processing the response signal further comprises determining information concerning individual ones of simultaneous modes of propagation of energy in the substance.

* * * * *